United States Patent [19]
Price et al.

[11] Patent Number: 5,609,638
[45] Date of Patent: Mar. 11, 1997

[54] REINFORCED POLYETHYLENE FOR ARTICULAR SURFACES

[75] Inventors: Howard C. Price, Wendell, N.C.; Steve T. Lin, Fort Wayne; Michael E. Hawkins, Columbia City, both of Ind.; Jack E. Parr, Arlington, Tenn.

[73] Assignee: Zimmer, Inc., Warsaw, Ind.

[21] Appl. No.: 346,125

[22] Filed: Nov. 29, 1994

[51] Int. Cl.$^6$ .................................................. A61F 2/30
[52] U.S. Cl. .................................. 623/18; 623/16; 623/20
[58] Field of Search .................................. 623/16, 18, 19, 623/20, 22, 23, 66

[56] References Cited

U.S. PATENT DOCUMENTS

| | | | |
|---|---|---|---|
| 4,055,862 | 11/1977 | Farling . | |
| 4,195,368 | 4/1980 | Patrichi | 623/18 |
| 4,221,623 | 9/1980 | Heissler et al. | 156/169 |
| 4,356,571 | 11/1982 | Esper et al. . | |
| 4,892,552 | 1/1990 | Ainsworth et al. | 623/23 |
| 4,902,297 | 2/1990 | Devanathan | 623/16 |
| 4,978,360 | 12/1990 | Devanathan | 623/66 |
| 5,064,439 | 11/1991 | Chang et al. | 623/66 |
| 5,079,825 | 1/1992 | Matsui et al. | 29/520 |
| 5,084,051 | 1/1992 | Tormala et al. | 606/77 |
| 5,163,962 | 11/1992 | Salzstein et al. | 623/23 |
| 5,181,930 | 1/1993 | Dumbleton et al. | 623/23 |
| 5,192,330 | 3/1993 | Chang et al. | 623/22 |
| 5,219,363 | 6/1993 | Crowninshield et al. | 623/23 |
| 5,236,457 | 8/1993 | Devanathan | 623/16 |

FOREIGN PATENT DOCUMENTS 2231800  11/1990  United Kingdom .

OTHER PUBLICATIONS

U.S. Application 07/321,049.
U.S. Application 07/689.674.
U.S. Application 08/101,337.
U.S. Application 08/250,238.

*Primary Examiner*—David Isabella
*Attorney, Agent, or Firm*—Cary R. Reeves

[57] ABSTRACT

An articular component has a fibrous structure wherein the fibers are oriented normal to the articular surface. Wear debris reduction is attributed to the increased strength of fibers over bulk material and to the abrasion resistance associated with abrading a fiber bundle on the fiber tips. This is similar to the abrasion resistance seen in a household broom which is subjected to abrasion across the tips of the broom bristles. Reduced cold flow is attributed to the increased strength and stiffness of fibers over bulk material.

7 Claims, 2 Drawing Sheets

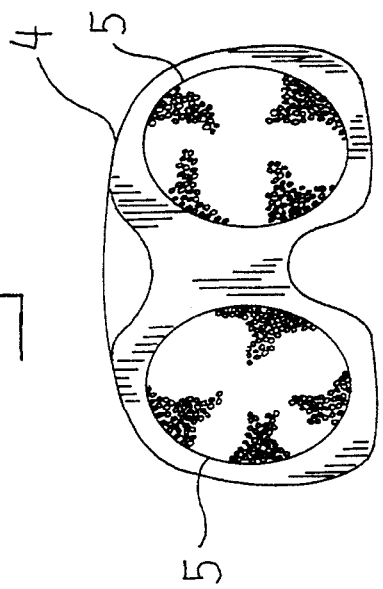
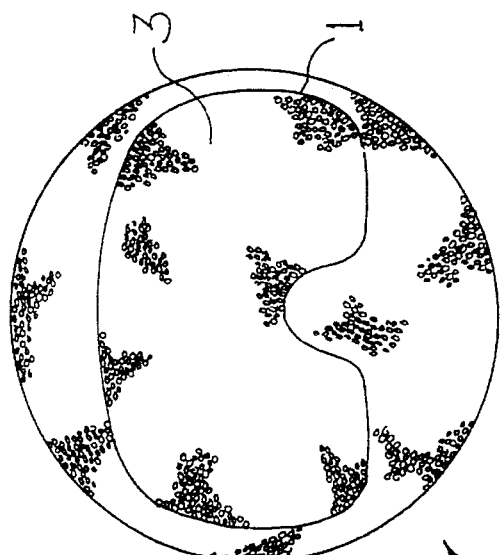
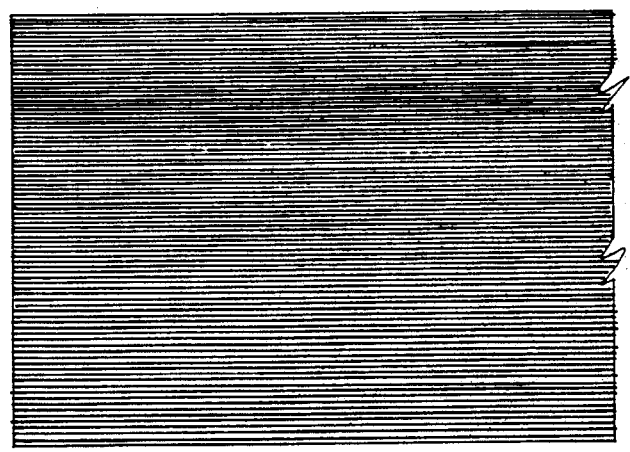
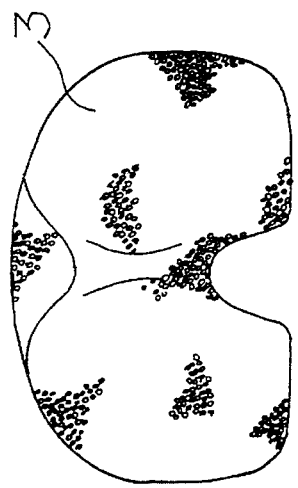

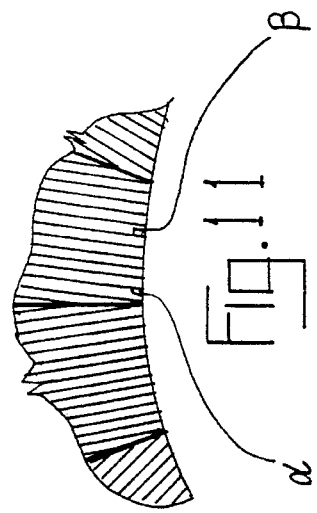
Fig. 11
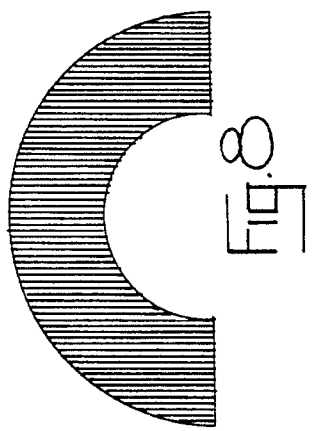
Fig. 8
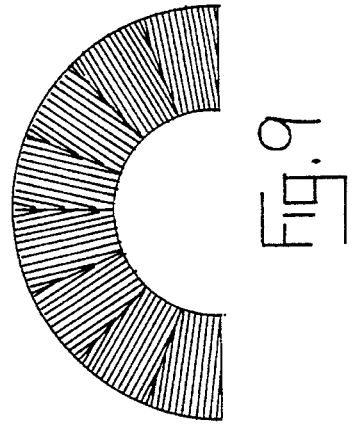
Fig. 9
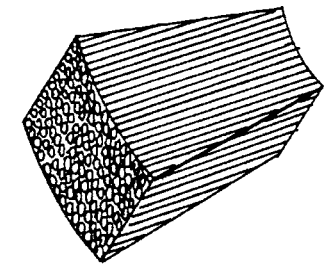
Fig. 10
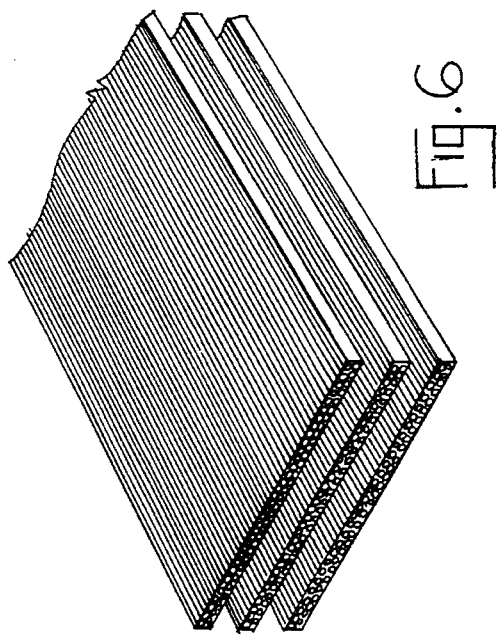
Fig. 6
Fig. 7

REINFORCED POLYETHYLENE FOR ARTICULAR SURFACES

BACKGROUND OF THE INVENTION

The present invention relates to materials for use as articular surfaces of prosthetic joint components. More particularly, it relates to reinforced polyethylene for articular surfaces.

Researchers have developed prosthetic joint replacements for all of the major skeletal joints of the human body. These prosthetic joints are used to replace degenerating or traumatized joints and thereby reduce pain and restore function. Most prosthetic joints currently available comprise a biologically compatible metal such as Ti—6Al—4V alloy or Cobalt-Chromium-Molybdenum alloy on one side of the joint and ultra high molecular weight polyethylene (UHMWPE) on the opposing side. The combination of metal and UHMWPE works well as a low friction articulating pair. However, there has been some concern over the biocompatability of fine particles of UHMWPE wear debris. This has led researchers to investigate ways of reducing the wear debris generated by metal on UHMWPE articulation while continuing to take advantage of the low friction and biocompatibility of bulk UHMWPE. In addition, UHMWPE will deform under load in a process known as cold flow. It is therefore desirable to control cold flow in order to provide dimensional stability and prevent the thinning of articular components to the point of breakage or wear through.

SUMMARY OF THE INVENTION

The present invention reduces the wear debris associated with metal on UHMWPE articulation and reduces the amount of cold flow exhibited by UHMWPE articular components. These results are achieved by providing an articular component having a fibrous structure wherein the fibers are oriented normal to the articular surface. Wear debris reduction is attributed to the increased strength of fibers over bulk material and to the abrasion resistance associated with abrading a fiber bundle on the fiber tips. This is similar to the abrasion resistance seen in a household broom which is subjected to abrasion across the tips of the broom bristles. Reduced cold flow is attributed to the increased strength and stiffness of fibers over bulk material.

BRIEF DESCRIPTION OF THE DRAWINGS

FIG. 1 is a top plan view of an articular component according to the present invention.

FIG. 2 is a side view of the articular component of FIG. 1.

FIG. 3 is a side view of a bar of consolidated fibers according to the present invention.

FIG. 4 is an end view of the consolidated fibers of FIG. 3.

FIG. 5 is a top plan view of an alternative articular component according to the present invention.

FIG. 6 is a perspective view of a plurality of thin sheets of consolidated fibers according to the present invention.

FIG. 7 is a perspective view of the sheets of FIG. 6 after having been consolidated into a block.

FIG. 8 is a side sectional view of another alternative articular component according to the present invention. No section lines are shown so as to make the view clearer.

FIG. 9 is a side sectional view of another alternative articular component according to the present invention. No section lines are shown so as to make the view clearer.

FIG. 10 is an expanded perspective view of one of the segments comprising the alternative articular component of FIG. 9.

FIG. 11 is an expanded side sectional view showing the fiber orientation at the articular surface of the alternative articular component of FIG. 9.

DETAILED DESCRIPTION OF THE INVENTION

FIGS. 1 and 2 depict a tibial articular component 1 made according to the present invention. The component comprises fibers, such as UHMWPE, which were first consolidated into a solid bar 2 as shown in FIGS. 3 and 4. The component 1 is then machined from the bar so that the fibers are oriented normal to the articular surface 3 of the component 1. Articular surfaces are not generally perfectly planar. Therefore, the fibers may not be perfectly normal at all points on the surface or even at any point on the surface. However, it is desirable to orient the fibers so that they are approximately normal to the principle areas of articulation. The principle areas of articulation are defined as the areas on the articular surface where the highest compressive loads are experienced during normal articulation. Another way of expressing the fiber orientation is that the fibers should advantageously be approximately parallel to the joint load axis. Since this axis also moves with articulation, the fibers should be parallel to the axis orientation at which maximum compressive loads occur during normal articulation. For a tibial articular component, the fibers should be oriented so that upon implantation of the component in a human body, the fibers will be approximately parallel to the axis of the tibia. In this way, when a femoral component articulates on the tibial component 1, the femoral component will glide across the surface 3 on the ends of the UHMWPE fibers.

The bar 2 of unidirectional UHMWPE fibers can be made by compressing and heating tows of UHMWPE fiber in order to consolodate them into a bar. Alternatively, UHMWPE fiber can be consolidated into sheets and then the sheets stacked and consolidated until the required thickness is achieved as shown in FIGS. 6 and 7. Another alternative is to pull a bundle of fibers through a heated die to consolodate them into a bar. In any of these methods, it may be advantageous to include UHMWPE powder with the fibers in order to help bind the fibers together and to fill spaces around the fibers. Also, in any method used, it is necessary that the heat and pressure be controlled so that the fibers do not melt into a homogeneous mass and thus loose the advantageous properties of the fibers. In other words, sufficient heat and pressure must be used to adhere the fibers to one another but not so much heat and pressure that the fibers cease to exist as fibers.

An alternative embodiment of a tibial articular component 4 according to the present invention is shown in FIG. 5. In this embodiment, only the principle areas of articulation contain unidirectional fibers. Inserts 5 are formed as described above and then the inserts 5 are incorporated into the articular component 4. One method of incorporating the inserts is by forming holes in a tibial articular component comprising bulk UHMWPE and then placing the inserts into the holes and then bonding the component and inserts with heat and pressure. Another method of incorporating the inserts is by placing the inserts and UHMWPE powder in a compression mold and consolidating the powder and inserts into a solid part with heat and pressure.

Joints other than knee joints can be made according to this invention. FIG. 8 depicts an acetabular articular component of a prosthetic hip joint made from a bar of unidirectional UHMWPE fibers. In an acetabular component, the fibers should be oriented so that they will be normal to the articular surface in the region of principle articulation. As with the tibial articular component, the acetabular articular component could be made with inserts at the region of principle articulation. An alternative acetabular component is shown in FIG. 9. In this component, the fibers are more nearly normal to the articular surface over a greater area of the articular surface than was the case in the acetabular component of FIG. 8. In a spherical acetabular component, articular loads are transmitted along radial lines running through the geometric center of the articular surface. An articular component with fibers approximately normal to the articular surface may be made by first forming wedge-shaped segments of unidirectional fibers with the fibers at the center of the segments normal to the articular surface as shown in FIGS. 10 and 11. These segments could be cut from a consolidated block of unidirectional fibers such as shown in FIG. 7. The segments would then be placed together in a spherical mold and consolidated into a unitary component with heat and pressure. In FIG. 11 it can be seen that the fibers at the center of each segment are normal to the articular surface, as shown by the angle α and that the fibers become less normal to the articular surface the further the fibers are from the center of the segment as indicated by the angle β. However, by forming the acetabular component from a plurality of segments, the fibers are approximately normal over the entire articular surface.

EXAMPLE

UHMWPE molding powder was sprinkled onto a rectangular mandrel measuring 4×7×0.5 inches and SPECTRA™ 900 UHMWPE fiber manufactured by Allied Signal Corporation was wound onto the mandrel. More UHMWPE powder was sprinkled over the wound fiber and the prepared mandrel was placed into a rectangular mold cavity. A plunger was placed on top of the mandrel and the fibers were molded at 312° F. with a one hour soak and a one hour hold to form a thin sheet of consolidated unidirectional fibers. 3×0.5 inch rectangles were cut from this thin sheet. The rectangles were stacked, with the fibers parallel, and placed in a cold mold. 1667 psi pressure was applied to the mold and the temperature was raised to 306° F. over a 20 minute warmup period and then maintained for a 15 minute soak period. The pressure was then increased to 1933 psi and held for 15 minutes. The mold was allowed to cool and the molded bar was removed. Oval inserts were cut from the molded bar and then placed into oval holes formed in the areas of principle articulation of an UHMWPE articular component. The inserts and articular component were consolidated into a single part at 1000 psi while the temperature was raised to 310° F. over a 20 minute warmup period and then maintained for a 60 minute soak period. The pressure was then raised to 2000 psi and held for 60 minutes. The finished part had unidirectional fibers normal to the articular surface located in the areas of principle articulation. Specimens made according to this example should have higher wear resistance and less cold flow then specimens made of homogeneous UHMWPE.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. An articular component of a prosthetic joint implant for the human body, the component comprising a body having an articular surface, the body including elongated fibers extending to and having terminating ends defining the articular surface, said fibers being oriented approximately normal to the articular surface.

2. The articular component of claim 1 wherein the fibers are consolidated to form inserts and said inserts are disposed in said body such that the fibers within each insert are oriented substantially normal to the articular surface.

3. The articular component of claim 1 wherein the component is a tibial component of a knee joint prosthesis for placement on a tibia and most of the fibers contained in the body are oriented parallel to one another such that the fibers are disposed parallel to the axis of the tibia when the component is placed on the tibia.

4. The articular component of claim 1 wherein the articular surface is non-planar and the component comprises a plurality of wedge-shaped segments, each segment comprising parallel consolidated fibers, the fibers of adjacent segments not being parallel, the segments being joined together to form said body which defines said articular surface wherein the fibers are approximately normal to the non-planar articular surface.

5. The articular component of claim 1 wherein said body is formed entirely from consolidated parallel fibers.

6. The articular component of claim 1 wherein the body has an articular component thickness measured normal to the articular surface and further wherein the fibers extend from the articular surface across the articular component thickness.

7. The articular component of claim 1 wherein the fibers are ultra high molecular weight polyethylene fibers which have been consolidated into a solid mass of fibers oriented approximately normal to the articular surface.

\* \* \* \* \*